(12) United States Patent
DiMaria-Ghalili et al.

(10) Patent No.: US 9,814,339 B2
(45) Date of Patent: Nov. 14, 2017

(54) DEVICE TO MEASURE AND MONITOR DRINKING AND EATING HAVING A CUP HOLDER WITH A DIGITAL CAMERA

(71) Applicant: Drexel University, Philadelphia, PA (US)

(72) Inventors: Rose Ann DiMaria-Ghalili, Jenkintown, PA (US); Kambiz Pourrezaei, Gladwyne, PA (US); Ahmad Pourshoghi, Tehran (IR)

(73) Assignee: Drexel University, Philadelphia, PA (US)

(*) Notice: Subject to any disclaimer, the term of this patent is extended or adjusted under 35 U.S.C. 154(b) by 103 days.

(21) Appl. No.: 14/909,020

(22) PCT Filed: Jul. 31, 2014

(86) PCT No.: PCT/US2014/049238
§ 371 (c)(1),
(2) Date: Jan. 29, 2016

(87) PCT Pub. No.: WO2015/017702
PCT Pub. Date: Feb. 5, 2015

(65) Prior Publication Data
US 2016/0166096 A1     Jun. 16, 2016

Related U.S. Application Data

(60) Provisional application No. 61/861,132, filed on Aug. 1, 2013.

(51) Int. Cl.
*A47G 23/02* (2006.01)
*G06Q 50/24* (2012.01)
(Continued)

(52) U.S. Cl.
CPC ......... *A47G 23/0216* (2013.01); *G01F 23/20* (2013.01); *G01F 23/292* (2013.01);
(Continued)

(58) Field of Classification Search
CPC ........ A47G 23/0216; G01F 23/20; B60Q 3/20
(Continued)

(56) References Cited

U.S. PATENT DOCUMENTS

| 4,523,083 A | 6/1985 | Hamilton |
| 6,425,862 B1 | 7/2002 | Brown |

(Continued)

OTHER PUBLICATIONS

International Preliminary Report on Patentability for PCT/US2014/049238, dated Feb. 2, 20165. 7 pages.
(Continued)

*Primary Examiner* — Que T Le
(74) *Attorney, Agent, or Firm* — Joseph E. Maenner; Maener & Associates, LLC

(57) ABSTRACT

In described embodiments, the present invention is a cup assembly including a cup holder having a base having a microcontroller, weight sensor and accelerometer incorporated therein, a handle extending upwardly from the base, and a camera support extending upwardly from the base. The camera support supports a digital camera. The digital camera is electronically coupled to the microcontroller. A cup is removably insertable into the cup holder. A method of using the cup assembly is also disclosed.

20 Claims, 9 Drawing Sheets

(51) Int. Cl.
  *G01F 23/292* (2006.01)
  *G01N 9/02* (2006.01)
  *G01N 21/03* (2006.01)
  *G01N 21/3577* (2014.01)
  *G01N 21/51* (2006.01)
  *G01F 23/20* (2006.01)
  *G06F 19/00* (2011.01)
  *G01N 21/53* (2006.01)

(52) U.S. Cl.
  CPC ............... *G01N 9/02* (2013.01); *G01N 21/03* (2013.01); *G01N 21/3577* (2013.01); *G01N 21/51* (2013.01); *G06F 19/3475* (2013.01); *G06Q 50/24* (2013.01); *G01N 21/532* (2013.01); *G01N 2009/024* (2013.01)

(58) Field of Classification Search
  USPC .......................................... 250/221, 239, 238
  See application file for complete search history.

(56) References Cited

U.S. PATENT DOCUMENTS

| | | |
|---|---|---|
| 6,978,221 B1 | 12/2005 | Rudy |
| 7,353,136 B2 | 4/2008 | Vock et al. |
| 7,459,713 B2 | 12/2008 | Coates |
| 7,581,442 B1 | 9/2009 | Dietz et al. |
| 9,539,942 B2 * | 1/2017 | Salter ................. H05B 37/0227 |
| 2001/0053283 A1 | 3/2001 | Hood et al. |
| 2004/0011807 A1 | 1/2004 | Knepler |
| 2004/0149020 A1 | 8/2004 | Lu et al. |
| 2005/0099304 A1 | 5/2005 | Humphrey |
| 2006/0000277 A1 | 1/2006 | Pietrorazio |
| 2008/0137486 A1 | 6/2008 | Czarenk et al. |
| 2008/0265146 A1 | 10/2008 | Coates |
| 2009/0239440 A1 | 9/2009 | Kang |
| 2011/0050431 A1 | 3/2011 | Hood et al. |
| 2012/0097567 A1 | 4/2012 | Zhao et al. |
| 2012/0247610 A1 | 10/2012 | Fuehrer |
| 2013/0029298 A1 | 1/2013 | Batsikouras |
| 2013/0157232 A1 | 6/2013 | Ehrenkranz |

OTHER PUBLICATIONS

International Search Report and Written Opinion for PCT/US2014/049238, dated Feb. 1, 2015. 12 pages.
http://www.hydracoach.com/applications/index.htm. 2004. 5 pages.
http://postcapes.com/smart-cup-drinke. Printed Jul. 10, 2013. 3 pages.
Etemadi, Mozzlyar et al. "SwigSmart". Dec. 2012. 7 pages.
http://mediacup.teco.edu/mitte.html. Printed Nov. 19, 2012. 6 pages.

\* cited by examiner

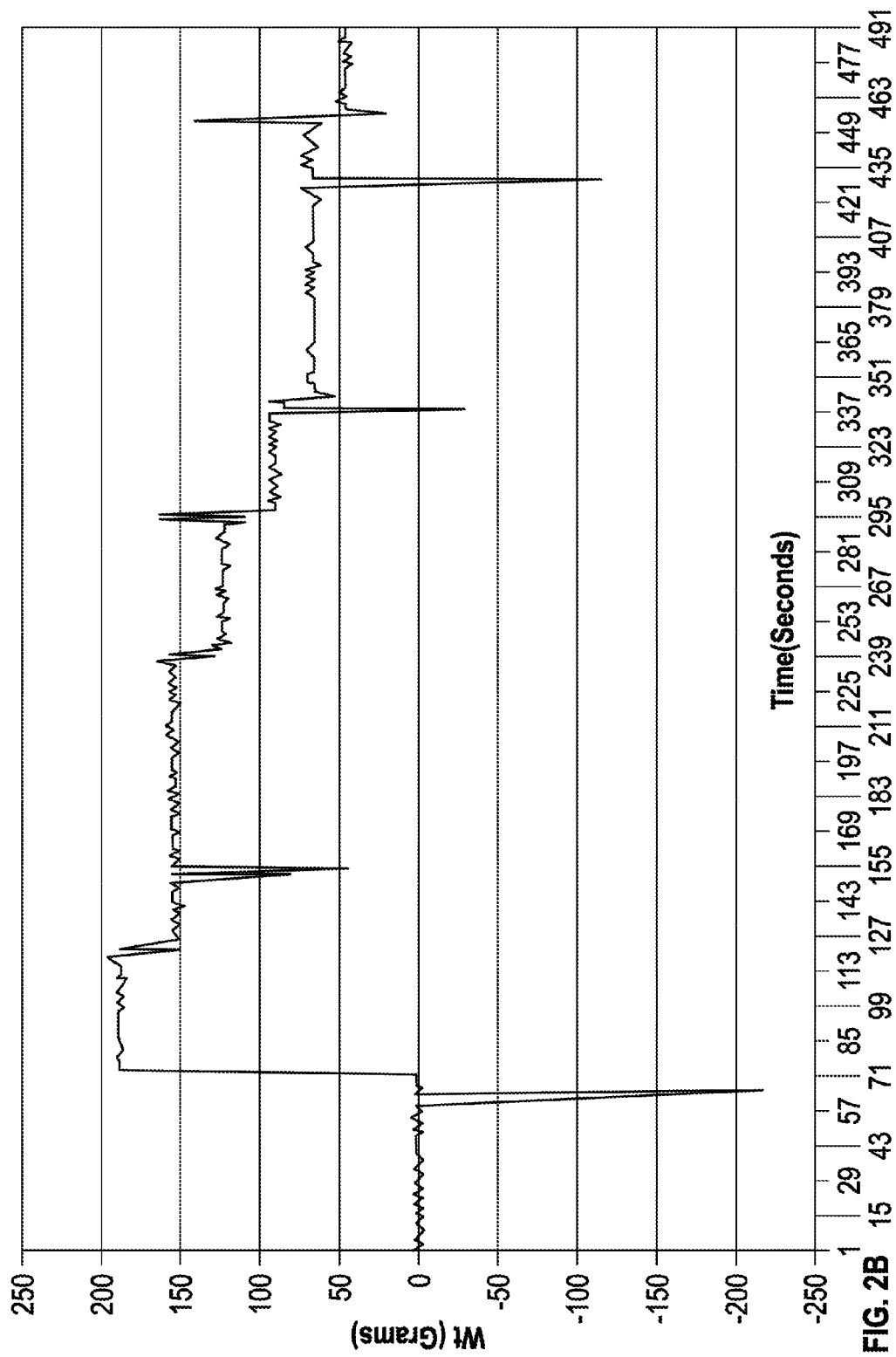

DEVICE TO MEASURE AND MONITOR DRINKING AND EATING HAVING A CUP HOLDER WITH A DIGITAL CAMERA

CROSS-REFERENCE TO RELATED INVENTION

The present application is a 371 OF Patent Cooperation Treaty Application PCT/US14/49238, filed on Jul. 31, 2014, which claims priority from U.S. Provisional Patent application Ser. No. 61/861,132, filed on Aug. 1, 2013, both of which are incorporated by reference herein in their entireties.

BACKGROUND OF THE INVENTION

Field of the Invention

The present invention relates to a liquid retaining device, and, in particular, to a liquid retaining device that may be used to measure, record, and monitor liquid intake.

Description of the Related Art

Malnutrition (i.e., undernutrition), a common geriatric syndrome in the United States, is found in older adults across the care continuum. Malnutrition is associated with adverse health outcomes that increase the cost of care, including hospital readmissions and institutionalization. It is difficult to manage malnutrition effectively because assessment of intake (including oral liquid nutrition supplements [ONS]) through either patient self-report or nurse's documentation is flawed. The only way to accurately measure the amount of ONS consumed is to record the amount (in cc) of liquid that remains after the ONS is consumed. This approach is time-consuming and labor intensive and can impact behavior if individuals self-record intake. Investigators report that healthcare personnel do not consistently document liquid intake in the medical record. Consequently, clinicians are left with unreliable nutritional data that renders decision making ineffective. There is therefore an unmet medical need for an unobtrusive technology that records and wirelessly monitors malnourished older adults' liquid intake. This technology can be used in other situations that require monitoring liquid intake during drinking events including hydration states (dehydration, overhydration, euhydration) or weight management. Furthermore, the technology can also be used to monitor food consumed during eating.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention provides a cup assembly including a cup holder having a base having a microcontroller incorporated therein, a handle extending upwardly from the base, and a camera support extending upwardly from the base. The camera support supports a digital camera. The digital camera is electronically coupled to the microcontroller. A cup is removably insertable into the cup holder.

In another embodiment, the present invention provides a method of using the cup assembly described above and monitoring consumption of the fluid from the cup.

In yet another embodiment, the present invention provides a method of classifying type of liquid. The method comprises steps of providing a liquid in a transparent container; transmitting a light having a wavelength of between about 200 nm and about 1500 nm into the liquid; detecting optical properties and scattering of the light; determining the volume of the liquid in the transparent container; determining the weight of the liquid in the transparent container; calculating the density of the liquid in the transparent container based on the volume and the weight of the liquid; and determining the type of liquid based on the optical properties and the density of the liquid.

In another embodiment, the holder takes the shape of a tray or plate or place mat with the described microcontrollers embedded into the holder and a removably insertable tray or plate or place mat is placed into the holder.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 2B is a graph showing the drinking pattern of a moderately malnourished person with a moderate grip strength;

DETAILED DESCRIPTION OF THE INVENTION

Figure 1:
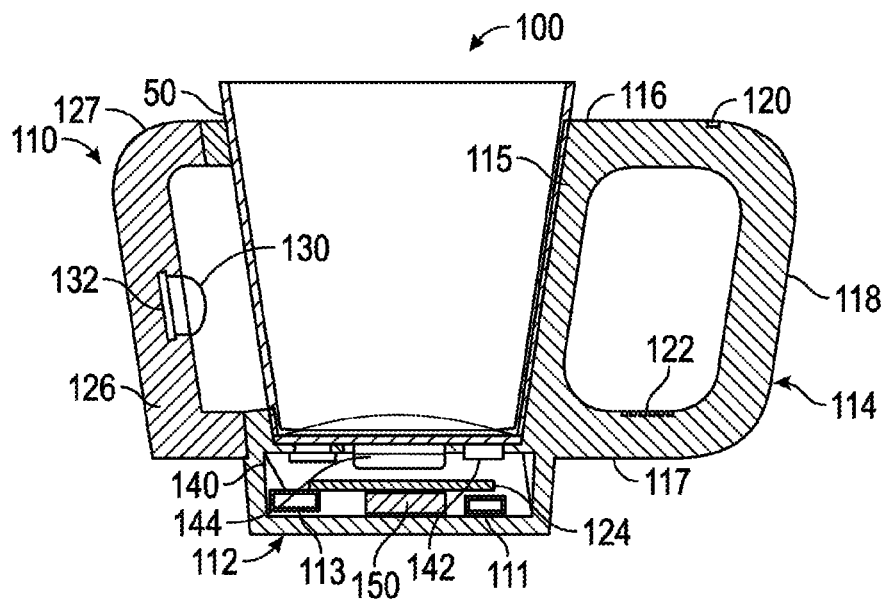
FIG. 1 shows a perspective view of a device used to measure liquid intake according to a first exemplary embodiment of the present invention.

Certain terminology is used in the following description for convenience only and is not limiting. The terminology includes the words above specifically mentioned, derivatives thereof and words of similar import. The embodiments described and illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

The present invention provides a liquid intake measurement device that may be used to provide information regarding the volume, time, rate, and identity of a liquid that is consumed from the liquid intake measurement device for a particular drinking episode, along with associated events. Such measurements assist healthcare providers with volume, time, and identity information of a liquid consumed for each drinking episode and associated events.

The present invention also provides a food intake measurement device that may be used to provide information regarding the amount, weight, time and identity of a solid food element(s) that is consumed from the food intake measurement device for a particular eating episode, along with associated events. Such measurements assist healthcare providers with volume, time, and identity information of food consumed for each eating episode and associated events. Alternatively, the present invention can be used to monitor patient adherence to consumption of other liquids, such as, for example, medications, oral contrast mediums, or other liquids to be ingested by a patient for procedures such as oral cathartics or clinical research trials that require patient/subject adherence to a form of liquid intake.

Information (data) collected from the measurement device is wirelessly transmitted to a remote location for processing. An algorithm harnesses this information to provide users (health care professionals, care recipients, care givers) of this device clinically relevant information. End users of the device can access the information through software applications (apps) or software programs developed for this purpose for use on a smart device or as an interface for personal computers, electronic health records, telehealth, remote patient monitoring systems, and other electronic systems that exchange information. Feedback loops are incorporated into the algorithm such that the user of the device (care recipient) receives auditory and visual prompts for drinking and eating.

Referring to the figures in general, the inventive device includes cup holder and a transparent disposable drinking cup. The cup holder includes electronic sensing and communication circuits. The inventive device is able to classify a liquid into one of several categories, is able to measure the rate and quantity of liquids consumed from the cup, and is sterilizable.

Figure 2:
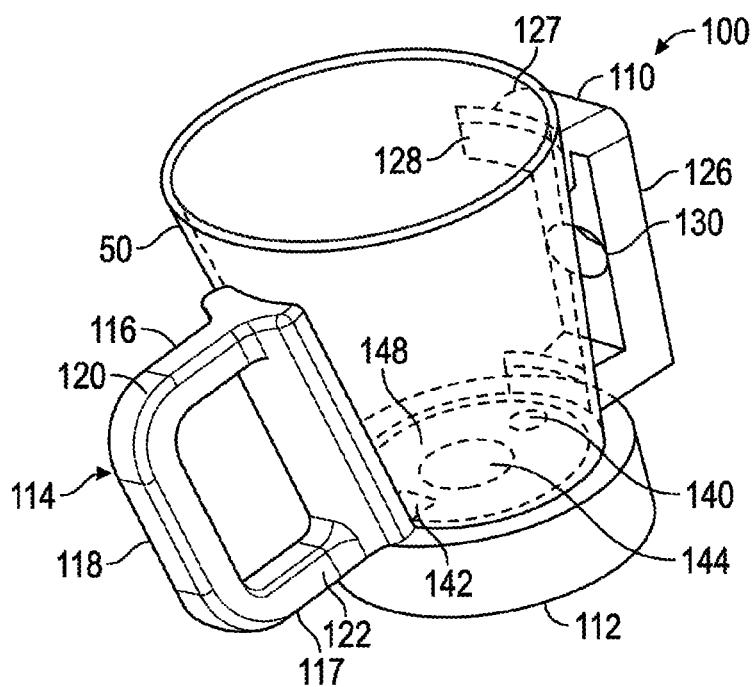
FIG. 2 shows a side elevational view, in section, of the device shown in FIG. 1.

Referring now to FIGS. 1 and 2, a liquid intake measurement cup assembly 100 according to an exemplary embodiment of the present invention is shown. Cup assembly 100 is in the form is of a cup holder 110 that accepts and retains a removable cup 50. Cup 50 can be disposable or reusable.

In an exemplary embodiment, removable cup 50 is constructed from a transparent or a translucent material such that light is able to pass through the walls of removable cup 50. Cup 50 can hold hot liquids as well as cold liquids. Additionally, cup 50 can be graduated so that a volume of liquid within cup 50 can be visually determined. Optionally, cup 50 can be fitted with a removable lid (not shown) to prevent spillage. In an exemplary embodiment, cup 50 may be a 10 ounce cup that is about 10 cm high and about 7 cm in diameter.

Cup assembly 100 includes cup holder 110 into which cup 50 may be removably inserted. Cup holder 110 includes a base 112 that houses a portion of the electronics that are used to operate cup assembly 100. In an exemplary embodiment, cup holder 110 is approximately 13 cm high at approximately 9 cm in diameter, with a weight of cup holder 110 (without cup 50) to be less than approximately 150 grams.

Cup holder 110 also includes a handle 114 that enables the user to lift cup assembly 100 without interfering with functions of cup assembly 100, as will be described herein. Handle 114 is coupled to base 112, and extends upwardly away from base 112. Handle 114 includes a generally concave cup engaging surface 115 that receives cup 50 and assists in preventing cup 50 from sliding laterally off of base 112 when cup 50 is inserted into cup assembly 100. Cup engaging surface extends from base 112 to the top of handle 114. Additionally, while cup holder 110 is shown as having a single handle 114, those skilled in the art will recognize that cup holder 110 can have a second handle (not shown). Additionally, cup holder 110 can be in the shape of a bottle or childrens' sippy cup. Cup 50 can be configured to fit into the particular shape of cup holder 110. Cup holder 110 may be constructed from a polymer, a composite material, or other suitable material such that cup holder 110 can be sterilized.

Handle 114 also includes a top portion 116 that extends generally horizontally outwardly from cup engaging surface 115, as well as a bottom portion 117, that also extends generally horizontally outwardly from cup engaging surface 115, parallel to top portion 116. A generally vertical grasping portion 118 extends generally vertically, or slightly away from the vertical, and connects top portion 116 with bottom portion 117. When cup assembly 100 is in use, the user grasps grasping portion 118 with his/her hand in order to pick up/move cup assembly 100.

A microphone 120 is incorporated into top portion 116 of handle 114, and is also electronically connected to a printed circuit board 124 located in base 112. Printed circuit board 124 may optionally be a flexible board in order to conform to the geometry of cup holder 110. In an exemplary embodiment, an application-specific integrated circuit (ASIC) chip may be used to integrate electronic elements that are presently mounted to printed circuit board 124.

Printed circuit board 124 receives and retains a digital transmission from microphone 120 corresponding to audio input received by microphone 120. In an exemplary embodiment, such audio input may be the voice of a user stating the type of liquid that is in cup 50.

A speaker 122 is incorporated into bottom portion 117 of handle 114, and is also electronically connected to printed circuit board 124. Printed circuit board 124 includes prerecorded audio messages digitally recorded thereon that are broadcast by speaker 122 to the user. Speaker 122 may generate an audio signal in the form of a simulated human voice, and can be used to prompt the user to speak into microphone 120. For example, speaker 122 may ask the user what type of fluid is in cup 50, prompting the user to speak the name of the fluid, which sound is picked up by microphone 120.

Both microphone 120 and speaker 122 are located on top portion 116 and bottom portion 117 of handle 114, respectively, so that, when the user grasps grasping portion 118, microphone 120 and speaker 122 are generally unobstructed and are able to receive and transmit audio, respectively.

A camera support 126 is located diametrically across cup holder 110 from handle 114. Camera support 126 is coupled to base 112 and extends upwardly away from base 112. A top portion 127 of camera support 126 includes a generally concave cup engaging surface 118 that assists cup engaging surface 115 in retaining cup 50 on to base 112.

A digital camera 130 is located approximately halfway up the length of camera support 126. An exemplary camera may utilize plastic wide-angle macro lens. Camera 130 is aligned on camera support 126 to face toward handle 114 so that, when cup 50 is mounted to cup assembly 100 and a liquid is poured into cup 50, camera 130 can be used during a drinking event.

In an exemplary embodiment, camera 130 utilizes an edge detection image processing tool, such as, for example, ImageJ, which was developed by the National Institutes of Health. While a single camera 130 is shown, those skilled in the art will recognize that multiple cameras may be incorporated into camera support 126 in order to provide three-dimensional image analysis. If more than one camera 130 is used, each camera 130 may be supported on a separate camera support 126, spaced around the periphery of cup 50, preferably at approximately 90° increments. Digital images provided by camera 130, along with known geometry of cup 50, are used to estimate liquid volume within cup 50.

Camera support 126 extends closely alongside cup 50 when cup is inserted into cup assembly 100 in order to discourage a user from grasping cup assembly 100 feet camera support 126 and inadvertently covering up camera 130 with his/her fingers.

A camera board 132 is electronically coupled to camera 130 as well as to printed circuit board 124. Camera board 132 transmits digital pictures from camera 130 to printed circuit board 124.

A top portion of base 112 also includes an "ON/OFF" switch 143 that powers on and off the electronics in cup assembly 100. Additionally, base 112 includes a contact switch 148 that is switched to an "on" position by inserting cup 50 into cup assembly 100. As cup 50 engages contact switch 148, contact switch 148 turns on cup assembly 100. When cup 50 is removed from cup holder 110, contact switch 148 switches to an "off" position, and turns off cup assembly 100 in order to conserve battery power.

Base 112 also includes weight sensor for example a load cell 144 that senses when fluid is added to cup 50. Another exemplary weight sensor 144 is a piezoelectric pressure sensor, such as the Honeywell TruStability Standard Accuracy Silicon Ceramic Series sensor. In an exemplary embodiment, weight sensor 144 can detect a 5 cubic centimeter (cc) change in weight and has an accuracy of better than 99%. The weight of liquid in cup 50 transmits an electronic signal to printed circuit board 124, which in turn activates electronic devices within cup assembly 100. By measuring the weight of liquid in cup 50, along with the known volume of liquid in cup 50 based on the information provided by camera 130, the density (mass/volume) of the liquid in cup 50 can be calculated.

Further, base 112 includes a light source, such as an LED 140, that transmits a light upward from base 112 and into cup 50. In an exemplary embodiment, LED 140 is an Everlight Standard LED having a 400-600 nm wavelength. Those skilled in the art, however, will recognize that the wavelength can be other values, including, but not limited to, 200-1500 nm.

A light detector 142 receives and measures reflected and scattered light from LED 140. In an exemplary embodiment, light detector 142 is a Vishay Optical Detector or a Texas Instruments OPT 101. Both LED 140 and light detector 142 are electronically coupled to printed circuit board 124. Light detector 142 is used to detect reflected light from LED 140, which can be used to measure and calculate light absorption in the liquid. The measurement of light absorption may then be used to assist in determining the type of liquid in cup 50.

Base 112 also includes an accelerometer 111 that measures movement of cup 50 and determines whether cup 50 has been dropped (high acceleration) or simply picked up for drinking (low acceleration). An exemplary accelerometer 111 can be a "Shake & Wake". When accelerometer 111 detects the low acceleration indicative of drinking, printed circuit board 124 transmits a "wake-up" signal to weight sensor 144, light detector 142, and camera 130 to begin recording data. Base 112 also includes a five degree gyroscope 113 that measures motion along three orthogonal axes (i.e., X, Y, Z axes), as well as two angles. Information obtained from gyroscope 113 can be used with accelerometer 111 to assist in distinguishing a normal drinking event from a spillage. Using gyroscope data, the angle of cup can be determined at any time during the drinking event or any other activities. Additionally, gyroscope 113 can also be used to assess the strength of the hand (i.e., steadiness) holding cup holder 110. Such strength measurement may provide medical information about the changes in a user's improvement or decline of overall physical strength.

Figure 2A:
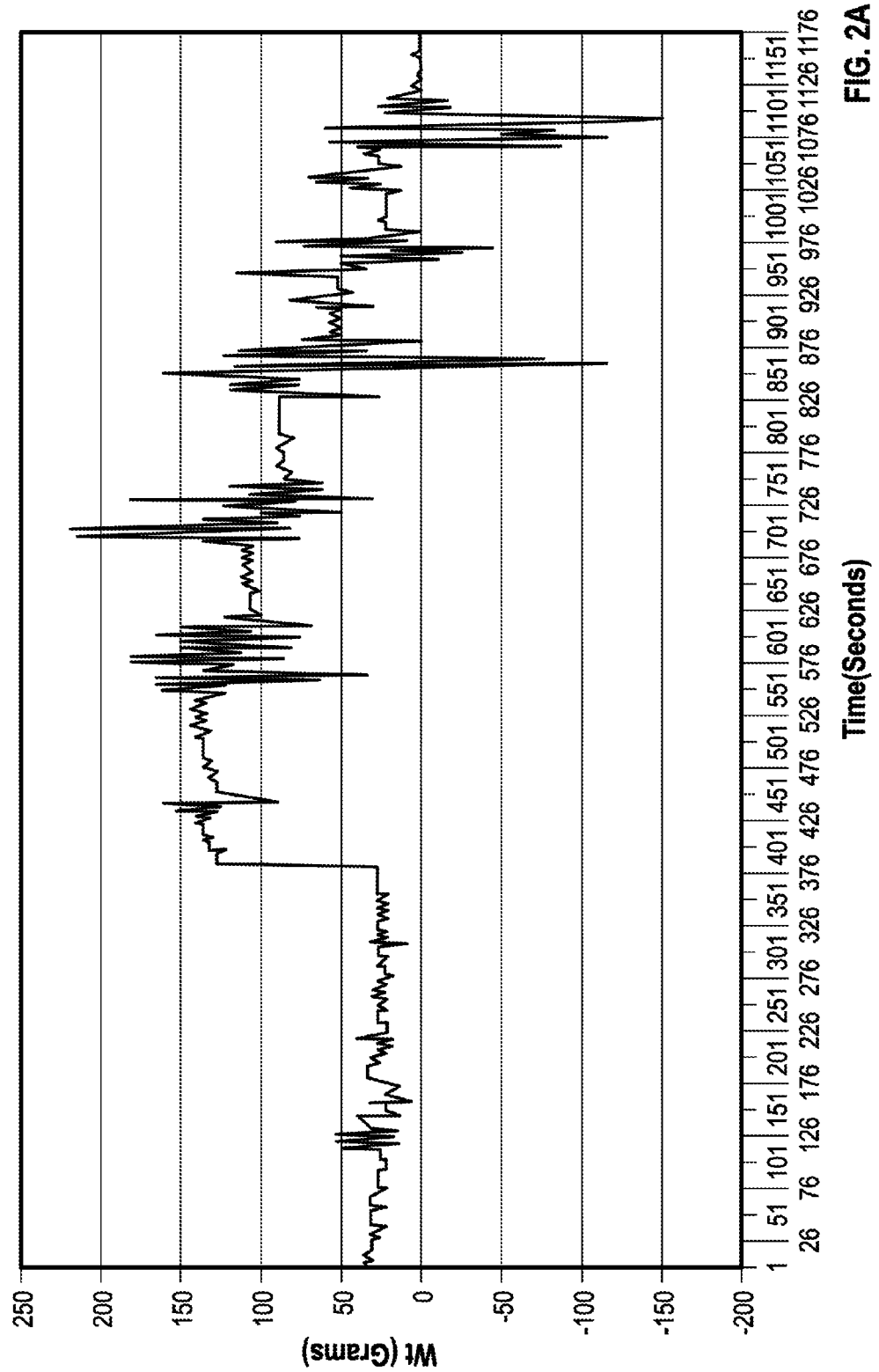
FIG. 2A is a graph showing the drinking pattern of a moderately malnourished person with a weak grip strength.

FIGS. 2A and 2B are graphs showing the drinking pattern of a moderately malnourished person with a weak grip strength and a moderate grip strength, respectively. The X axis represents time in seconds, and the Y axis represents the weight of cup 50, cup holder 114, and the fluid in cup 50, in grams. The spikes in the graph results represent shakiness or noise in the data. The spikes can be filtered using a low band pass or Kalman filter (not shown). As expected, the patient with a weak grip strength (as shown in FIG. 2A) has relatively more shakiness than the patient with a moderate grip strength (as shown in FIG. 2B)

Figure 2C:
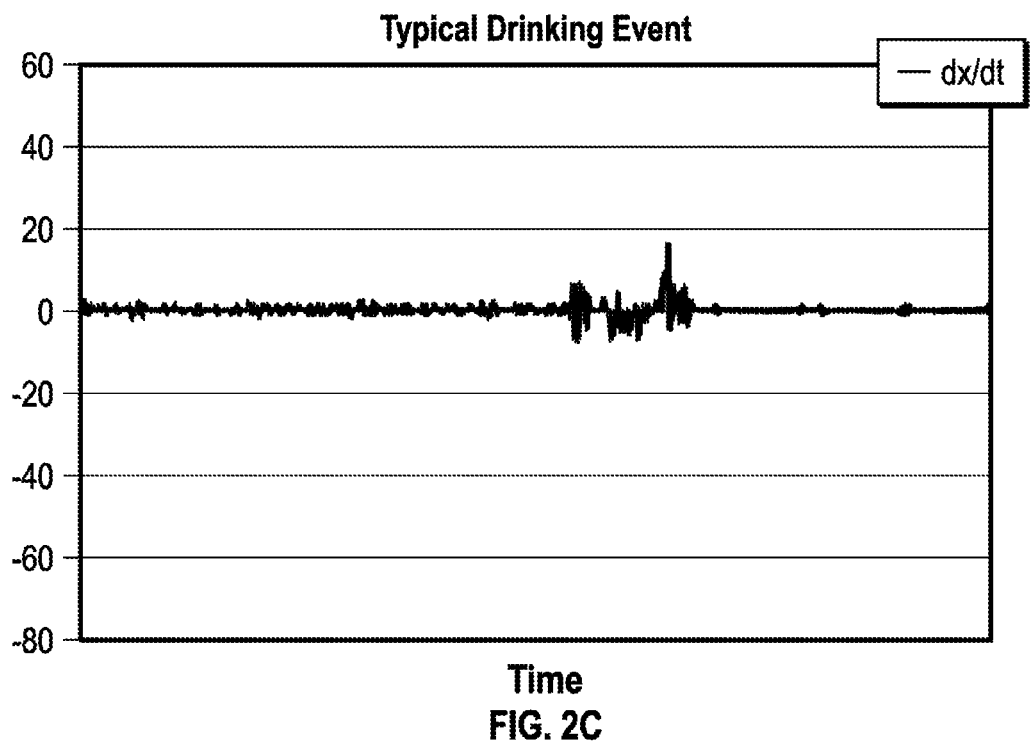
FIG. 2C is a graph showing a derivative of accelerometer data along an X axis for normal drinking event.
Figure 2D:
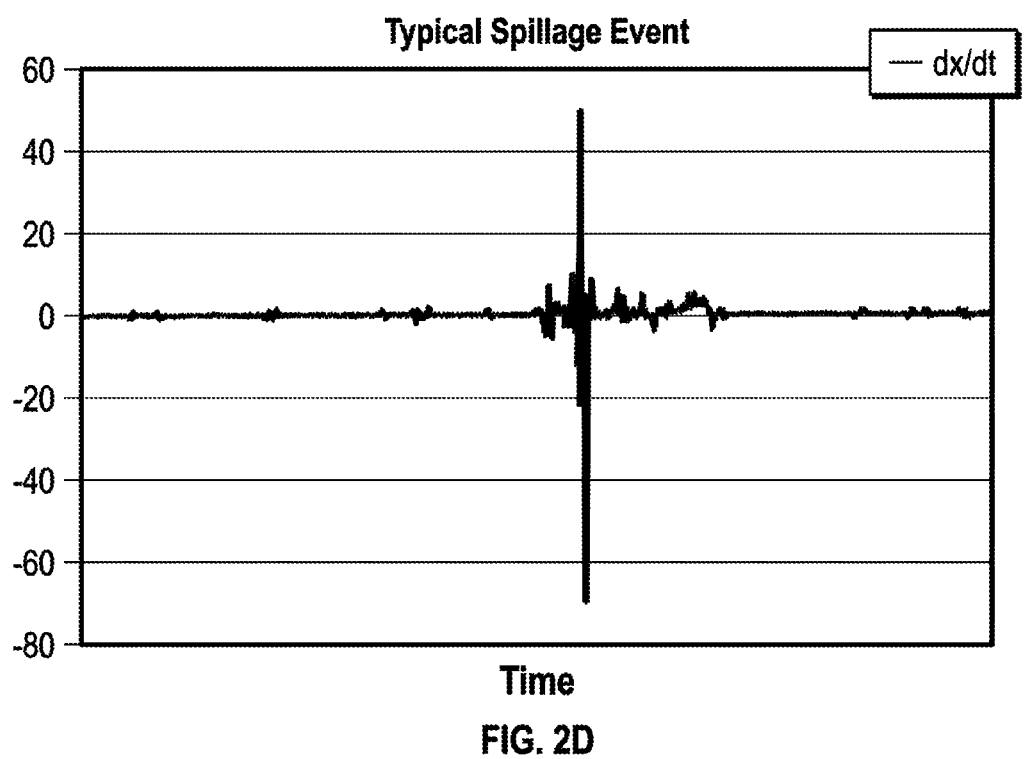
FIG. 2D is a graph showing a derivative of accelerometer data along an X axis for a spillage event.

FIGS. 2C and 2D illustrate data obtained from accelerometer 111 that shows how an event can be distinguished between a typical drinking event (FIG. 2C) and a spillage event (FIG. 2D). FIGS. 2C and 2D are graphs of the derivative of data from accelerometer 111 in the x-axis. It has been determined by the inventors that by choosing a proper threshold, the significant difference in the value of "X" clearly indicates a distinction between a drinking event and a spillage event.

When cup 50 has been removed from cup assembly 100 or otherwise disposed of, contact switch 148 is deactivated, turning off the remaining electronic components. In an exemplary embodiment, the remaining electronic components are not immediately turned off. A time delay may be incorporated into printed circuit board 124 so that the remaining electronic components remain activated for a predetermined period of time in order to obtain a transmit information to printed circuit board 124 as may be required.

Printed circuit board 124 includes a microcontroller incorporated therein that enables at least some limited data and analysis calculations therein. Further, printed circuit board 124 also includes a clock that is used to timestamp the start and stop times of treating episodes and events.

Printed circuit board 124 may include a Bluetooth chip (not shown) incorporated therein to enable data from printed circuit board 124, including audio, photographic, weight, light, and other such data, to be downloaded from printed circuit board 124 to a remote server or other electronic device 52 (shown in FIG. 3), for later data analysis. To meet HIPAA requirements, it is desired to use it wireless protocol based on IEEE standard 11073-00101-2008 (Point of Care Medical Device Communication, Guidelines for Use of RF Wireless Technology), which is approved for hospital use. Also, in accordance with HIPAA requirements, al information obtained from cup assembly 100 is processed using a HIPAA-compliant secured web-based dashboard (not shown.

A rechargeable battery 150 is located within base 112 and is used to power electronic components described above. Battery 150 is electrically coupled to printed circuit board 124, which in turn powers the other electronic components. While the exemplary battery 150 is a rechargeable battery, those skilled in the art will recognize that battery 150 may be replaceable batteries instead of a rechargeable battery. In an exemplary embodiment, battery 150 can be two 3.7 V cells, 210 mAh. Battery 150 can be recharged by directly plugging battery 150 into a recharging source (not shown). Alternatively, battery 150 can be recharged by placing base 112 on a wireless charging device (not shown), utilizing inductive charging, radio charging, and/or resonance charging or other known or as yet unknown methods of wireless charging.

Figure 3:
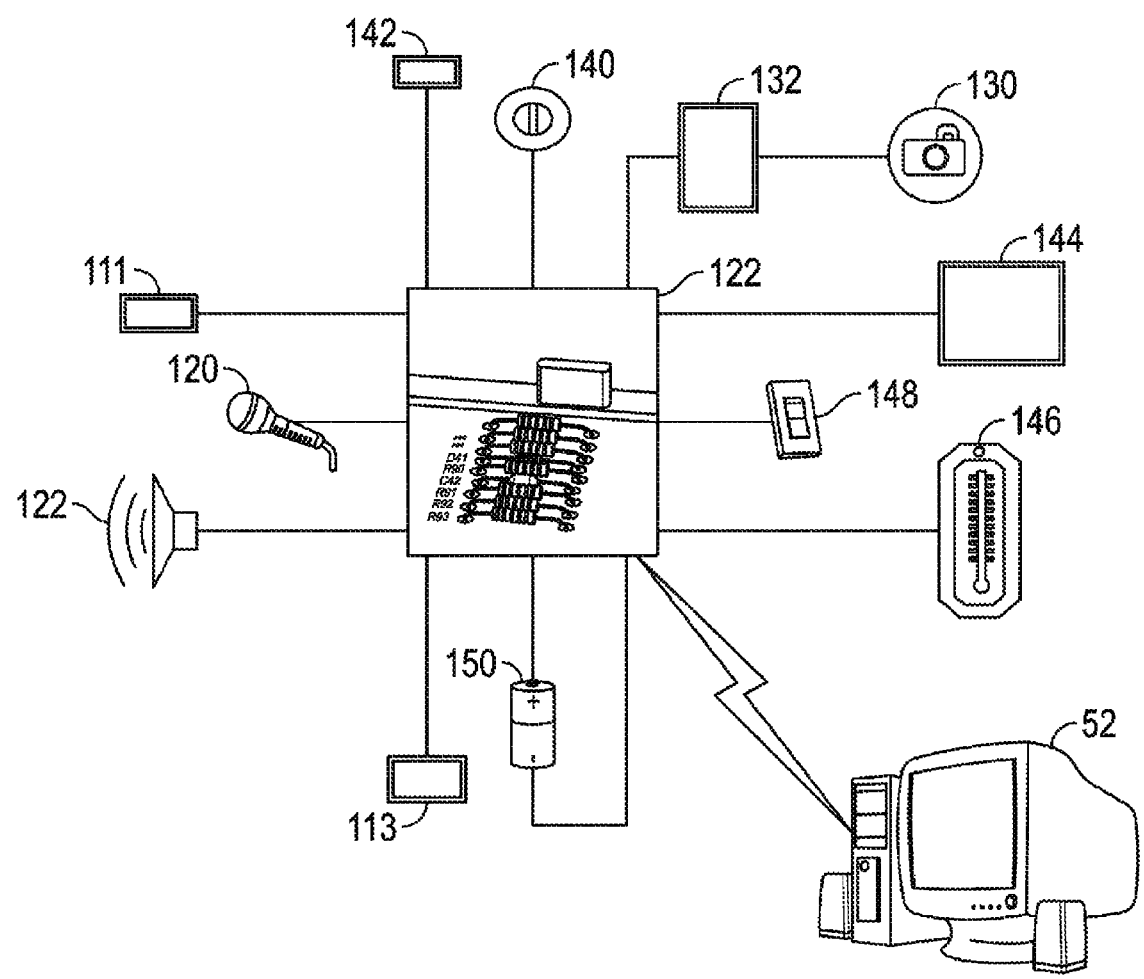
FIG. 3 shows a schematic drawing of an exemplary electronic circuit used with the device shown in FIG. 1.
Figure 4:
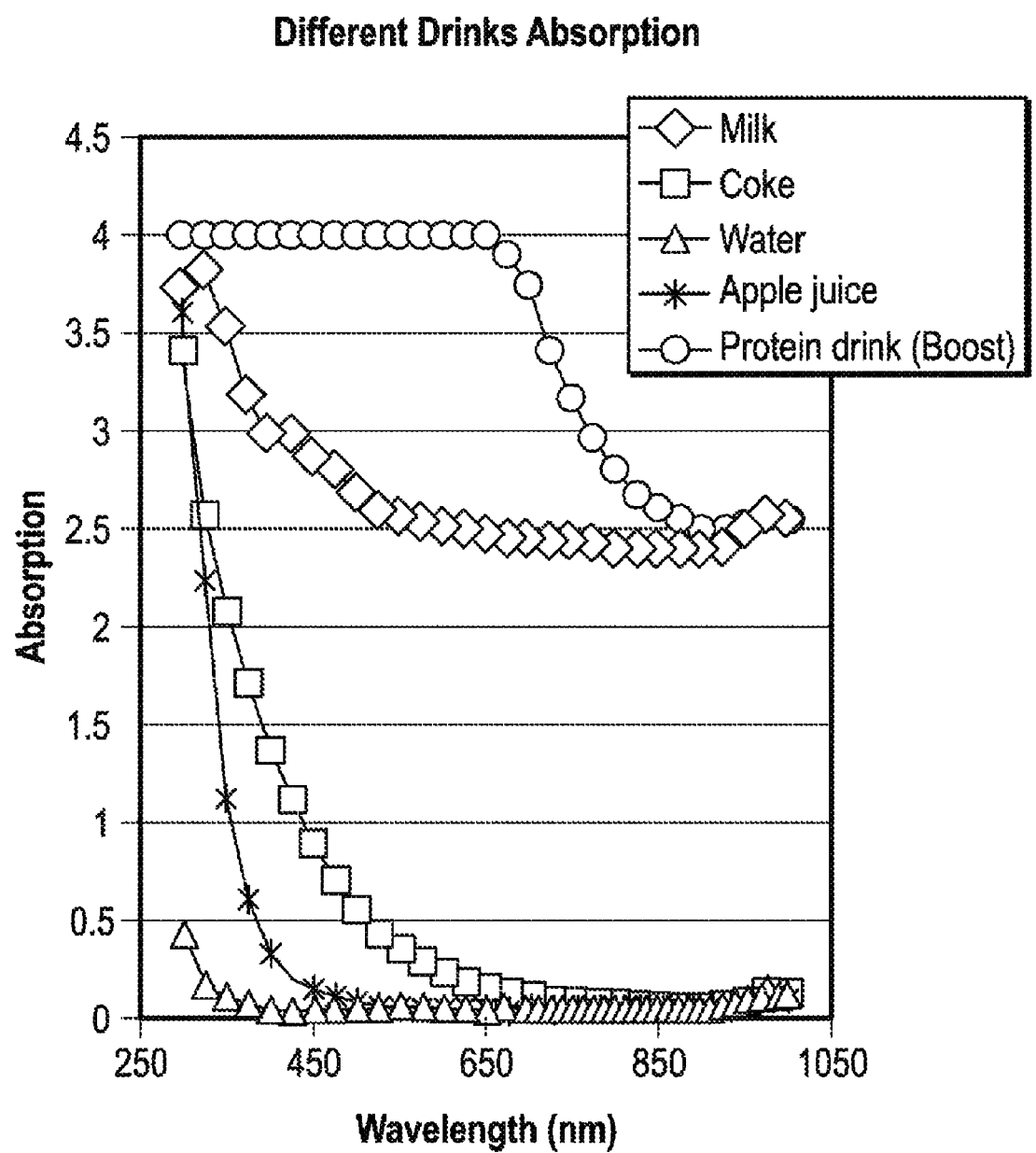
FIG. 4 is a graph showing light absorption versus wavelength for different types of fluids.

FIG. 3 shows a schematic drawing of an exemplary configuration of electronic devices disclosed above for use with cup assembly 100. Those skilled in the art will recognize that other types of devices and other electronic configurations may be used. Cup assembly 100 can be used to identify and classify various drinks for automated evaluation of the nutritional content of liquid within cup 50 that are being consumed by patients. It has been determined by the inventors that, based solely on optical properties, such as optical absorption and scattering, and density of liquid, five commonly consumed liquids can be easily distinguished. FIG. 4 shows a graph of optical absorption versus wavelength for milk, a caramel colored carbonated beverage such as Coca-Cola, water, apple juice, and a protein drink, such as Boost. The optical absorption and scattering of each of these five drinks are sufficiently different, such that the type of drink can be readily distinguished by its optical absorption and scattering over optical wavelengths of between about 400 nm and about 600 nm, and more specifically, at about 450 nm.

Figure 5:
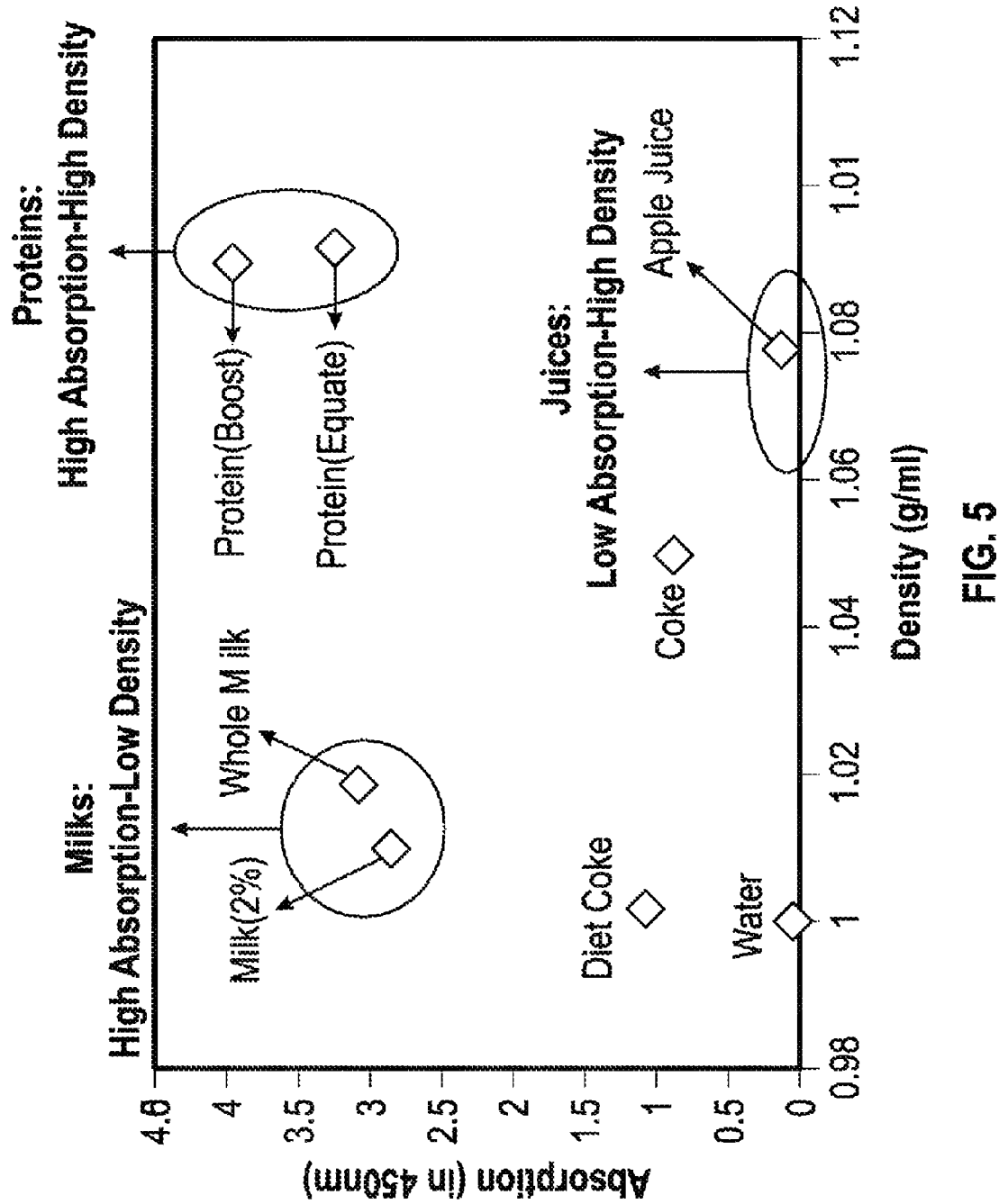
FIG. 5 is a graph showing light absorption versus liquid density for different types of fluids.

Additionally, as shown FIG. 5, by adding density measurements of different liquids and measuring their optical absorption and scattering at 450 nm, liquids within cup 50 can be classified into one of five categories (water, juice, soda, milk, and protein-calorie supplement). As a result of measuring the optical absorption and scattering and the density of the liquid in cup 50, the type of liquid in cup 50 can be determined and electronically stored on printed circuit board 124.

To operate assembly 100, cup 50 is placed securely into cup holder 110, activating contact switch 148. Liquid is then poured into cup 50, which initiates a new drinking episode that may include several drinking events spaced out over an extended period of time. When the weight is no longer changing (i.e., when cup 50 is full), printed circuit board 124 activates microphone 120, speaker 122, camera 130, LED 140, and light sensor 142 to initiate the simultaneous measurement of data once the change in weight stops.

Figure 6:
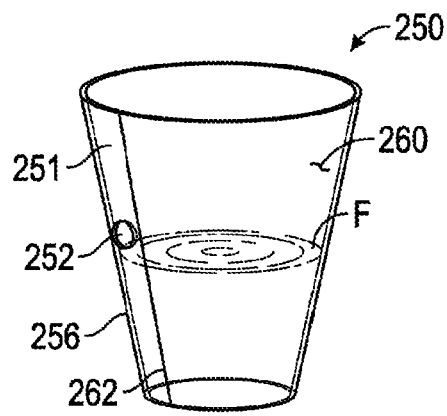
FIG. 6 is a side elevation view of a device used to measure liquid intake according to a second exemplary embodiment of the present invention.

LED 140 transmits the light upward from base 112, through bottom of cup 50, and into the liquid. Light sensor 142 measures the optical absorption and scattering of the light. Weight sensor 144 measures the weight of the fluid in cup 50 and camera 130 detects the volume of the fluid in cup 50. Based on these parameters, and as shown in FIGS. 5 and 6, the type of fluid in cup 50 can be determined. Optionally, a thermometer 146 can be incorporated into cup holder 110 such that thermometer 146 is in contact with cup 50. Thermometer 146 is used to measure the temperature of the liquid within cup 50.

Speaker 122 provides an auditory prompt asking the user what type of drink is being consumed. The user says the name of the drink, which is picked up by microphone 120 and stored electronically on printed circuit board 124. The recording of the name of the drink is a redundancy added in addition to the determination of the type of fluid in cup 50 based on light absorption and density parameters as described above. Additionally, data generated on the volume, time, and identity of the liquid as calculated via the graphs shown in FIGS. 5 and 6 is stored on printed circuit board 124.

The user (not shown) begins drinking from cup 50. A drinking episode begins when a change in weight is sensed by weight sensor 144. A change in the weight of cup 50 is sensed by weight sensor 144. The volume of fluid drunk during the preceding drinking episode can be calculated by subtracting the present weight of cup 50 from the initial weight and dividing by the density of the fluid.

Optionally, when activated, printed circuit board 124 generates an auditory message to the user via speaker 122 and asks the user simple question such as "what are you drinking?". If the user response "soda" into microphone 120, the next verbal prompt will be "regular or diet?" The user's response assists in determining calorie intake and other features. Those skilled in the art will recognize that the auditory elements (microphone 120 and speaker 122) of assembly 100 may be disabled if desired. Further, printed circuit board 124 can generate an auditory message to the user via speaker 122 to remind the user to drink from cup 50.

Using assembly 100, a clinician can monitor the volume and type of fluid consumed, as well as using known information about the liquid to calculate calories and protein consumed, and temporal drinking patterns (i.e., drink faster slow, drink with meals or between meals, time of day, etc.). It is desired that assembly 100 be used for each drinking event, with cup 50 properly inserted into cup holder 110 during the drinking event.

Instead of relying on light sensor 142 and weight sensor 144 to detect the volume of the fluid in cup 50, a cup 250, shown in FIG. 6 in alternative embodiment of the present invention, can be used. Cup 250 includes a float 252 located in a side passage 254 along a wall 256 of cup 250. Side passage 254 is in fluid communication with the inside volume 260 of cup 250 so that fluid within inside volume 260 also flows into side passage 254 such that float 252 floats on top of the fluid "F" within cup 250. In an exemplary embodiment, the fluid communication is provided near the bottom of cup 250 by way of a fluid communication opening 262. Fluid communication opening 262 is smaller than the diameter of float 252 so that float 252 can not pass through fluid communication opening and into inside volume 260 of cup 250.

The location of float 252 within side passage 254 can be determined by at least one of several methods. When the location of float 252 is known, the volume of the fluid "F" can then be readily calculated. A first method that can be used to determine the location of float 252 includes using camera 130 to locate float 130. Alternatively, float 252 can be at least partially metallic or magnetic, with a magnetic reader (not shown) built into cup holder 110 and electronically connected to printed circuit board 124. Those skilled in the art will recognize that other methods and arrangements for determining the location of float 252 within side passage 254 can be used.

Figure 7:
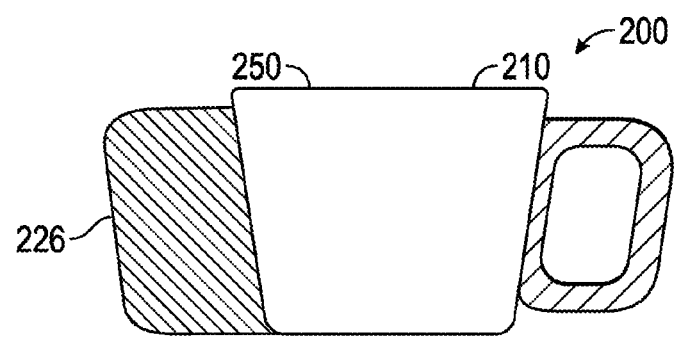
FIG. 7 shows a side elevational view of a device used to measure liquid intake according to an alternative exemplary embodiment of the present invention.
Figure 8:
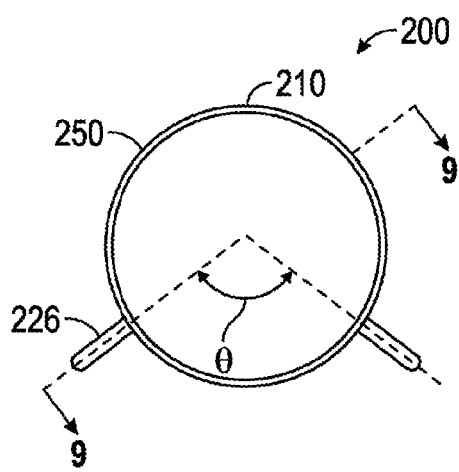
FIG. 8 shows a top plan view of the device shown in FIG. 7.
Figure 9:
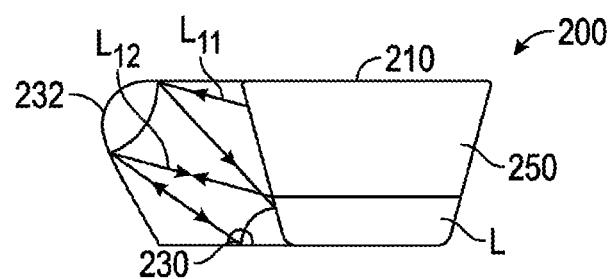
FIG. 9 shows a sectional view of the device shown in FIG. 8, taken along lines 9-9 of FIG. 8.

In an alternative embodiment of the present invention, shown in FIGS. 7-9, a cup assembly 200 is shown. Cup assembly 200 uses a camera 230 and a mirror 232 embedded in a camera support 226 that is part of a cup holder 210. Cup holder 210 also includes a handle 214 that a user can grasp to use cup assembly 200. As shown in FIG. 8, a plane of handle 214 and camera support 226 intersect at an angle $\Theta$. In an exemplary embodiment, $\Theta$ is approximately 120 degrees. It is desired that $\Theta$ is not 180 degrees so that light can more easily pass through a transparent cup 250 to camera support 226.

As shown in FIG. 9, mirror 232 is a convex mirror that is angled so that incident light $L_{f1}$ and $L_{f2}$ that passes through cup 250 above the level of liquid L in cup 250 reflects off mirror 232 and to camera 230 so that camera 230 can record the amount of light passing through cup 250. Based on the size of cup 250, the amount of light recorded by camera 230 can be calibrated to determine the volume of cup 250 that does not have liquid and, by subtracting the total volume of cup 250, determine the amount of liquid in cup 250.

Alternatively, instead of camera 230, cup assembly 200 can use a light meter (not shown) or other device to determine the amount of light passing through cup 250 that is reflected off mirror 232.

In another alternative embodiment, cup 50 can be prepackaged with a known type and quantity of fluid. Cup 50 includes indicia, such as a barcode or other type of optical readout (not shown), on an exterior thereof that can be read by a sensor on cup holder 110, such as camera 130. Alternatively, if cup 50 and cup holder 110 are prepackaged together, the barcode can be applied to cup holder 110. The barcode can provide information such as the identity of the liquid within cup 50, as well as volume and nutritional information about the liquid. A caregiver can scan the barcode with a handheld scanner (not shown) and transmit the scanned information to remote device 52.

Alternatively, cup 50 and/or cup holder 110 can include a passive RFID chip (not shown). The information on cup 50 that is read by the RFID sensor is transmitted to the microcontroller in printed circuit board 124, which can be preprogrammed with the type of fluid inside cup 50, thereby eliminating the need to determine the optical absorption and scattering properties and density of the fluid to determine the type of fluid inside cup 50. Such barcode, RFID, or other types of information can also be used for prepared meals, such as, for example, to monitor the consumption of home delivered meals.

In yet another alternative embodiment, cup 50 can include a plurality of passive sensors located a predetermined positions on the exterior of cup 50. Corresponding active sensors on base 110, coupled to printed circuit board 124, "look" for the passive sensors. The presence or absence of one or more of the passive sensors, as determined by a respective active sensor, indicates the type of fluid in cup 50. For example, for a maximum of four (4) sensors, 16 different permutations of the presence or absence of the sensors are available, which provides for 16 different types of prepackaged fluid that can be provided in cup 50.

Figure 10:
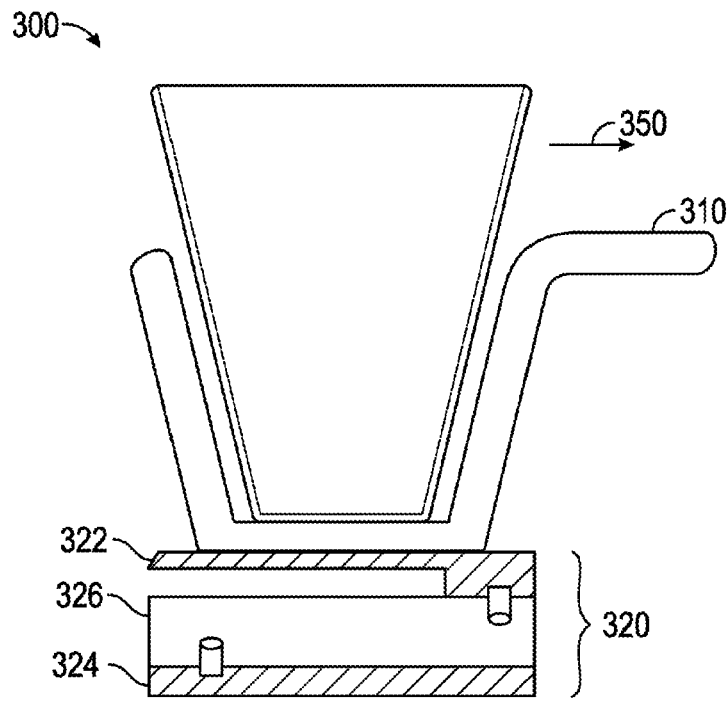
FIG. 10 shows a side elevational view of an alternative embodiment of a cup assembly and base according to the present invention.
Figure 11:
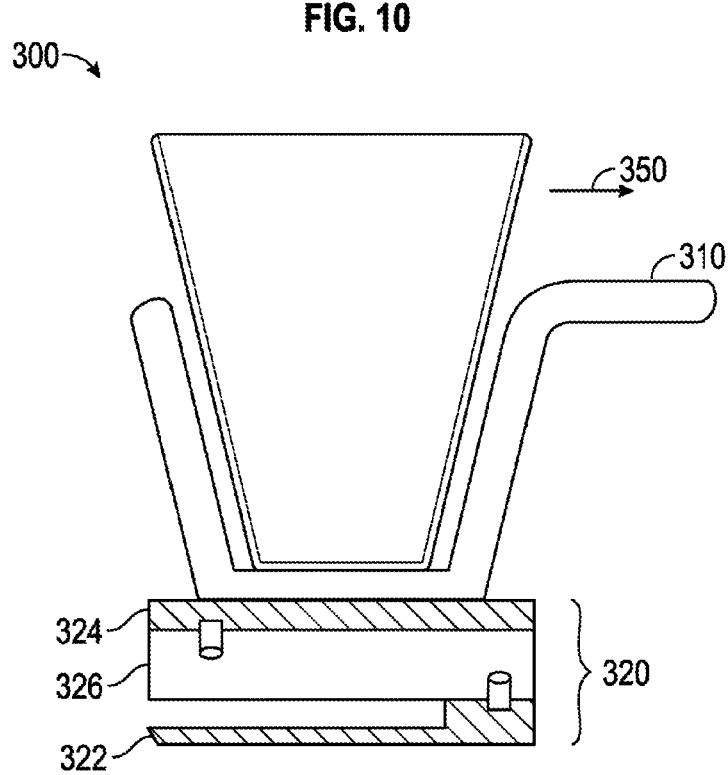
FIG. 11 shows a side elevational view of the cup assembly, and base shown FIG. 10, with the base inverted.

FIG. 10 shows an alternative embodiment of a cup assembly 300 according to the present invention. Cup assembly 300 includes a cup 350 insertable into a cup holder 310. A base 320 on which cup holder 310 rests includes a top floating surface 322, a bottom fixed surface 324 and a load cell 326 located between top floating surface 322 and bottom fixed surface 324. Alternatively, as shown in FIG. 11, base 320 can be inverted such that cup holder 310 rests on fixed surface 324, with floating surface 322 beneath fixed surface 324, and load cell 326 between fixed surface 324 and floating surface 322. Load cell 326 can transmit weight information to a microprocessor, such as, for example, the microprocessor in printed circuit board 124.

While cup assemblies 100, 200, 300 are discussed above as being used in a clinical environment, those skilled in the art will recognize that cups 100, 200, 300 can be used in a home setting as part of a home tele-monitoring program that can monitor weight, blood pressure, heart rate, etc. Also, using such a tele-monitoring program, clinicians can provide feedback to the users in close to real time, such as through the web, text messages, cell phone apps, cell phone and/or landline phone.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A cup assembly comprising:
   a cup holder comprising:
      a base having a microcontroller incorporated therein;
      a handle extending upwardly from the base; and
      a camera support extending upwardly from the base, the camera support supporting a digital camera, the digital camera being electronically coupled to the microcontroller; and
   a cup removably insertable into the cup holder.

2. The cup assembly according to claim 1, further comprising a microphone incorporated into a top portion of the handle.

3. The cup assembly according claim 2, further comprising a speaker incorporated into a bottom portion of the handle.

4. The cup assembly according to claim 1, wherein the cup is insertable between the handle and the camera support.

5. The cup assembly according to claim 1, wherein the base further comprises a light source adapted to transmit light toward the cup and a light detector adapted to detect the light transmitted from the light source.

6. The cup assembly according claim 1, wherein the base further comprises a weight sensor adapted to detect the weight of fluid in the cup and to transmit weight information to microcontroller.

7. The cup assembly according claim 1, wherein the camera support comprises a concave cup engaging surface.

8. The cup assembly according claim 1, wherein the base further comprises a switch operable between an off position when the cup is removed from the cup holder and an on position when the cup is inserted into the cup holder.

9. The cup assembly according to claim 1, wherein the cup holder further comprises an accelerometer electronically coupled to the microcontroller, wherein the accelerometer transmits electronic information to the microcontroller to distinguish between the drinking event and the spillage.

10. The cup assembly according to claim 1, wherein the cup holder further comprises a gyroscope electronically coupled to the microcontroller, wherein the gyroscope transmits electronic information to the microcontroller to measure the angle of the cup and hand strength of a user.

11. The cup assembly according to claim 10, wherein the gyroscope comprises a five degree gyroscope.

12. The cup assembly according to claim 1, further comprising a base adapted to removably receive the cup holder, the base including a load cell incorporated therein.

13. The cup assembly according to claim 1, wherein the cup contains a fluid and wherein at least one of the cup and the cup holder comprises a barcode, the barcode containing electronic information about the fluid.

14. A method of monitoring the consumption of fluid from the cup assembly according to claim 1, the method comprising the steps of:
 (a) measuring the weight of a fluid in the cup;
 (b) measuring the volume of the fluid in the cup;
 (c) measuring optical properties of the fluid in the cup;
 (d) time stamping changes in the weight of the fluid in the cup;
 (e) repeating steps (a) and (b); and
 (f) storing the time and measured weight, volume, and optical properties of the fluid in a processor.

15. The method according claim 14, further comprising generating a first audio signal prior to step (d).

16. The method according claim 15, further comprising receiving a second audio signal and storing the second audio signal in the processor.

17. The method according claim 16, further comprising generating a third audio signal after step (d).

18. The method according claim 14, further comprising determining the type of the fluid based on steps (a)-(c).

19. The method according claim 18, further comprising storing the type of the fluid in the processor.

20. The method according claim 14, further comprising downloading the information from step (f) from the processor.

* * * * *